US012582595B2

(12) United States Patent
Pang et al.

(10) Patent No.: US 12,582,595 B2
(45) Date of Patent: Mar. 24, 2026

(54) SYSTEM AND METHOD FOR PRIMING EYE COSMETICS

(71) Applicant: L'ORÉAL, Paris (FR)

(72) Inventors: Christopher Pang, Nanuet, NY (US); Sylvie Poret-Fristot, Clark, NJ (US)

(73) Assignee: L'OREAL, Paris (FR)

( * ) Notice: Subject to any disclaimer, the term of this patent is extended or adjusted under 35 U.S.C. 154(b) by 249 days.

(21) Appl. No.: 18/379,398

(22) Filed: Oct. 12, 2023

(65) Prior Publication Data

US 2024/0033206 A1 Feb. 1, 2024

Related U.S. Application Data

(62) Division of application No. 17/038,026, filed on Sep. 30, 2020, now abandoned.

(51) Int. Cl.
| | |
|---|---|
| *A61K 8/891* | (2006.01) |
| *A61K 8/06* | (2006.01) |
| *A61K 8/26* | (2006.01) |
| *A61K 8/34* | (2006.01) |
| *A61K 8/36* | (2006.01) |
| *A61K 8/86* | (2006.01) |
| *A61Q 1/10* | (2006.01) |

(52) U.S. Cl.
CPC .............. *A61K 8/891* (2013.01); *A61K 8/062* (2013.01); *A61K 8/26* (2013.01); *A61K 8/345* (2013.01); *A61K 8/361* (2013.01); *A61K 8/86* (2013.01); *A61Q 1/10* (2013.01)

(58) Field of Classification Search
CPC .......... A61Q 1/10; A61K 8/891; A61K 8/062; A61K 8/26; A61K 8/345; A61K 8/361; A61K 8/86
See application file for complete search history.

(56) References Cited

U.S. PATENT DOCUMENTS

| | | | |
|---|---|---|---|
| 4,309,447 A | 1/1982 | Tsutsumi et al. | |
| 6,531,155 B1 | 3/2003 | Schade | |
| 2003/0003054 A1 | 1/2003 | McDonald et al. | |
| 2006/0275232 A1 | 12/2006 | Chevalier | |
| 2014/0193351 A1 | 7/2014 | Mohammadi | |
| 2014/0271511 A1* | 9/2014 | Mu ...................... A61K 8/8182 424/78.03 |
| 2017/0042778 A1 | 2/2017 | Carle | |
| 2019/0254938 A1 | 8/2019 | Hayakawa | |
| 2020/0028183 A1 | 1/2020 | Kim et al. | |
| 2020/0078287 A1* | 3/2020 | Fischer .................. A61K 47/32 |
| 2020/0085710 A1 | 3/2020 | Denda | |

FOREIGN PATENT DOCUMENTS

| | | |
|---|---|---|
| CN | 106361662 A | 2/2017 |
| FR | 2954116 A1 | 6/2011 |
| JP | H08310940 A | 11/1996 |
| JP | 2011132154 A | 7/2011 |

OTHER PUBLICATIONS

French Search Report and Written Opinion for corresponding French Application No. 201229, dated Jul. 22, 2021.
Wilfried Umbach: "Chapter 18", Kosmetik und Hygiene von Kopf bis FuB, Weinheim, XP855789993, pp. 316-328, Jan. 1, 2004.
Lennon, "Cosmetic Formulations Containing Emulium Mellifera", ip.com. ip.com Inc, r Jan. 8, 2014.

* cited by examiner

*Primary Examiner* — Jianfeng Song
(74) *Attorney, Agent, or Firm* — Meagher Emanuel Laks Goldberg & Liao, LLP

(57) ABSTRACT

Cosmetic compositions, and methods of use, where the cosmetic compositions are multi-purpose oil-in-water emulsions that contain (i) a surfactant system of high HLB surfactants and (ii) a high load of talc. The emulsions are capable of being used as a base for eye cosmetics, in order to enhance wear of eyeshadow and removal of mascara.

5 Claims, No Drawings

SYSTEM AND METHOD FOR PRIMING EYE COSMETICS

TECHNICAL FIELD

The present invention relates to cosmetic compositions, and specifically to cosmetic compositions containing a high HLB surfactants and a high load of talc that are capable of being used as a base for other eye cosmetics, in order to enhance wear of eyeshadow and removal of mascara.

BACKGROUND

Consumers of eye cosmetics desire products that provide long wear for the eye cosmetics, and allow those eye cosmetics to be removed easily, in addition to providing an aesthetic finish. As these are typically competing interests, consumers who wish good wear and easy removal may be required to purchase additional products to meet those needs—for example, a long-lasting mascara may need to purchase a special product to remove the eye cosmetic from the lashes. Given that eye cosmetics include eyeliners, eyeshadows, and mascaras, the proliferation of products that a consumer may require can quickly grow beyond a desirable quantity. Thus, a product that can reduce the number of required products by filling multiple roles—such as enhancing the wear of eyeshadow and removal of mascara—is desirable.

Many primers used in eye cosmetics are anhydrous. But these products tend to be difficult to remove. Emulsion products with talc have been used as eyeshadow primers, but the amount of talc in the products is low, for both aesthetic and performance reasons.

Thus, an emulsion-based primer, that can fill multiple roles, using high levels of talc, is novel and useful.

BRIEF SUMMARY

A first aspect of the present disclosure is drawn to a multipurpose eye makeup oil-in-water emulsion. The emulsion comprises at least 10% by weight of talc, and at least 3% by weight of one or more high HLB surfactants, which can be fatty alcohols (such as behenyl alcohol and/or cetyl alcohol) and/or fatty esters of polyethylene glycol (PEG) or glycerol. The high HLB surfactants may include a diester of stearic acid (such as polyglyceryl-6 distearate). In some embodiments, the emulsion comprises between 10% and 20% by weight of talc.

The emulsion may include one or more pasty compounds (such as shea butter or paraffin wax) in amounts less than 5% by weight. The emulsion may include other optional ingredients, including at least one silicone material (such as dimethicone, a dimethicone copolymer, or dimethiconol) or a hygroscopic agent (such as glycerin). Further, while talc may sometimes be considered a filler agent on its own, the emulsion may optionally include a secondary filler agent, such as stearalkonium hectorite. The emulsion may also be free or substantially free of a colorant.

A second aspect of the present disclosure is drawn to an eye makeup system or kit, which includes the disclosed multipurpose eye makeup oil-in-water emulsion, configured to be applied directly to eyelids, eyelashes, or both. The system or kit also includes an eyeshadow composition, a mascara composition, or both, configured to be applied over the emulsion. It is envisioned that any eyeshadow and/or mascara composition can be used, and such compositions are well known to those of skill in the art.

A third aspect of the present disclosure is drawn to a method for using the disclosed multipurpose eye makeup oil-in-water emulsion. The emulsion is provided, and then applied to an eyelid, eyelashes, or both. In preferred embodiments, the emulsion is applied to both eyelids and eyelashes. In some embodiments, an eyeshadow composition is applied to the eyelids over the emulsion. In some embodiments, a mascara composition is applied to the eyelashes over the emulsion.

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the terms "between [two numbers]" is intended to include those two numbers. For example, "x is between 1 and 2" is intended to cover $1 \leq x \leq 2$.

As used herein, the terms "include", "includes" and "including" are meant to be non-limiting.

As used herein, the term "high HLB surfactant" is intended to include any surfactant with a hydrophilic-lipophilic balance (HLB) greater than or equal to about 9, and preferably $\geq 9$. In some embodiments, all of the high HLB surfactants have HLB values $\geq 10$. In some embodiments, all of the high HLB surfactants have HLB values $\geq 11$. In some embodiments, the weighted HLB of all of the high HLB surfactants is $\geq 11$ (for example, if the composition comprises 1% of a 9 HLB surfactant and 4% of a 15 HLB surfactant, the weighted HLB would be 13.8). The HLB value can be determined according to GRIFFIN in J. Soc. Cosm. Chem. 1954 (volume 5), pages 249-256.

As used herein, the term "substantially free [of an ingredient]" means that the composition contains less than 1% of the identified ingredient.

Disclosed is a multipurpose eye makeup oil-in-water emulsion, adapted to being used as a primer for both mascara and eyeshadow in order to increase wear of the eyeshadow and allow a user to more easily remove mascara. The emulsion contains a high load of talc and a surfactant system with specific characteristics, including high HLB surfactants.

Talc

The talc may be coated or uncoated. A non-limiting example of a talc appropriate for the disclosed composition is that sold under the trade name Talc P-3® by the company Nippon Talc.

The talc used may have a particular size. While talc is typically not spherical in shape, particle size analyzers are often used to provide a size estimate. In such cases, the talc may be found to have a median diameter (D50)$\leq 7$ microns, $\leq 5$ microns, $\leq 3$ microns, or $\leq 2$ microns, and generally the D50 is $\geq 0.1$ microns, $\geq 1$ micron, or $\geq 1.5$ microns, and/or any combination thereof.

The emulsion contains at least 10% by weight of talc. The emulsion preferably contains between 10% and 50% by weight of talc, more preferably between 10% and 30% by weight of talc, and still more preferably between 10% and 20% by weight of talc.

High HLB Surfactants

According to preferred embodiments of the present invention, compositions further comprising at least one High HLB Surfactant are provided. Preferably, the compositions comprise at least two such surfactants, at least three such surfactants, or at least four such surfactants. "HLB" means hydrophile-lipophile balance.

The high HLB surfactant(s) should be fatty alcohols and/or fatty esters of polyethylene glycol (PEG) or glycerol.

As used herein, the term "fatty alcohol" includes an alcohol having an aliphatic tail, typically from 4 to 30 carbon atoms long. Fatty alcohols can be saturated, mono-unsaturated, poly-unsaturated, linear or branched. Examples of fatty alcohols useful in the present invention include, but are not limited to, lauryl alcohol (C12), tetradecanol (C14), pentadecanol (C15), cetyl alcohol (C16), stearyl alcohol (C18), oleyl alcohol (C18), eicosanol (C20) and behenyl alcohol (C22). One of skill in the art will appreciate that other fatty alcohols are useful in the present invention.

As used herein, the term "fatty ester" includes any ester made from a fatty acid to produce, for example, a fatty acid ester. In one embodiment, a fatty ester contains an A side (i.e., the carbon chain attached to the carboxylate oxygen) and a B side (i.e., the carbon chain comprising the parent carboxylate). In a preferred embodiment, the A side is contributed by an alcohol, and the B side is contributed by a fatty acid. Any alcohol can be used to form the A side of the fatty esters.

As used herein, the term "fatty acid" means a carboxylic acid having the formula RCOOH. R represents an aliphatic group, preferably an alkyl group. R will generally comprise between about 4 and about 22 carbon atoms. Fatty acids can be saturated, monounsaturated, or polyunsaturated.

These high HLB surfactants can be selected from nonionic, anionic, cationic and amphoteric surfactant agents. Preferably the surfactants are non-ionic.

Suitable surfactants of HLB greater than or equal to 9, used alone or as a mixture, include:

Fatty alcohols such as cetyl, steryl, and/or behenyl alcohol. In some embodiments, the high HLB surfactants comprise, consist essentially of, or consist of cetyl and behenyl alcohol. In some embodiments, the high HLB surfactants comprise fatty alcohols that consist of cetyl and behenyl alcohol. In some embodiments, the high HLB surfactants are free, or substantially free, of steryl alcohol. In some embodiments, the high HLB surfactants comprise, consist essentially of, or consist of cetyl alcohol. In some embodiment, the fatty alcohols comprise, consist essentially of, or consist of cetyl and behenyl alcohol. In some embodiment, the fatty alcohols comprise, consist essentially of, or consist of cetyl alcohol.

Fatty esters, in particular C8-C24, and preferably C16-C22, and polyethylene glycol (or PEG) (which can contain from 1 to 150 ethylene oxide units), such as the PEG-50 stearate or PEG-40 monostearate marketed under the MYRJ® brand name by Croda International.

Fatty esters, in particular C8-C24, and preferably C16-C22, and ethoxylated and/or propoxylated ethers of glycerol (which can contain from 1 to 150 ethylene oxide and/or propylene oxide units), such as the polyglyceryl-10 dipalmitate or polyglyceryl-6 distearate. In some embodiments, the high HLB surfactant comprises a fatty ester that consists of one or more diesters of stearic acid.

In some embodiments, the high HLB surfactant(s) are free or substantially free, of fatty esters.

According to preferred embodiments, high HLB surfactant(s) are present in the composition of the present invention in a total amount greater than or equal to 3%. In some embodiments, the high HLB surfactant(s) are present in a total amount ranging from about 3% to 15% by weight, more preferably from about 3% to about 10% by weight, more preferably from about 3% to about 8% by weight based on the total weight of the composition, including all ranges and subranges within these ranges.

Pasty Compounds

The composition according to the invention may further comprise at least one pasty compound.

A "pasty compound" in the sense of the present invention refers to a lipophilic fatty compound which exhibits a reversible solid/liquid state change and which, at a temperature of 23° C., comprises a liquid fraction and a solid fraction. Thus, pasty compounds include fatty compounds, or hydrocarbon-based waxes, that have a waxy and/or pasty consistency at 23° C. (e.g., shea butter, cocoa butter, and paraffin wax). This preferably includes complex fats containing nonsaponifiables and fatty acids, and having a melting point above 23° C. These materials are preferably not surfactants. In other words, the starting melting point of the pasty compound is less than 23° C. The liquid fraction of the pasty compound measured at 23° C. represents from 20% to 97% by weight of the pasty compound. This fraction that is liquid at 23° C. more preferentially represents from 25% to 85% and better still from 30% to 60% by weight of the pasty compound.

The liquid fraction by weight of the pasty compound at 23° C. is equal to the ratio of the enthalpy of fusion consumed at 23° C. to the enthalpy of fusion of the pasty compound.

The enthalpy of fusion consumed at 23° C. is the amount of energy absorbed by the sample to change from the solid state to the state that it has at 23° C., composed of a liquid fraction and a solid fraction.

The enthalpy of fusion of the pasty compound is the enthalpy consumed by the compound to change from the solid state to the liquid state. The pasty compound is said to be in the solid state when all of its mass is in solid form. The pasty compound is said to be in the liquid state when all of its mass is in liquid form.

The enthalpy of fusion of the pasty compound is equal to the area under the curve of the thermogram obtained using a differential scanning calorimeter (DSC), such as the calorimeter sold under the name MDSC 2920 by the company TA Instrument, with a temperature rise of 5 or 10° C. per minute, according to standard ISO 11357-3:1999. The enthalpy of fusion of the pasty compound is the amount of energy required to make the compound change from the solid state to the liquid state. It is expressed in Jig.

The liquid fraction of the pasty compound, measured at 32° C., preferably represents from 40% to 100% by weight of the pasty compound and better still from 50% to 100% by weight of the pasty compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same manner as the enthalpy of fusion consumed at 23° C.

The pasty compound preferably has a hardness at 20° C. ranging from 0.001 to 0.5 MPa and preferably from 0.002 to 0.4 MPa.

The hardness is measured according to a method of penetration of a probe into a sample of compound and in particular using a texture analyzer (for example the TA-XT2i from Rheo) equipped with a stainless-steel cylinder 2 mm in diameter. The hardness measurement is performed at 20° C. at the center of five samples. The cylinder is introduced into each sample, the penetration depth being 0.3 mm. The hardness value recorded is that of the maximum peak.

The pasty compound may be selected from synthetic compounds and compounds of plant origin. A pasty compound may be obtained by synthesis from starting materials of plant origin.

The pasty compound is advantageously selected from: (i) lanolin and derivatives thereof such as lanolin alcohol, oxyethylenated lanolins, acetylated lanolin, lanolin esters such as isopropyl lanolate, and oxypropylenated lanolins; (ii) polymeric or non-polymeric silicone compounds, for instance polydimethylsiloxanes of high molecular masses, and polydimethylsiloxanes with side chains of the alkyl or alkoxy type containing from 8 to 24 carbon atoms, especially stearyl dimethicones; (iii) polymeric or non-polymeric fluoro compounds; (iv) vinyl polymers, especially olefin homopolymers, olefin copolymers; (v) hydrogenated diene homopolymers and copolymers; (vi) linear or branched oligomers which are homopolymers or copolymers of alkyl (meth)acrylates preferably containing a $C_8$-$C_{30}$ alkyl group; (vii) oligomers which are homopolymers and copolymers of vinyl esters containing $C_8$-$C_{30}$ alkyl groups; (viii) oligomers which are homopolymers and copolymers of vinyl ethers containing $C_8$-$C_{30}$ alkyl groups; (ix) lipid-soluble polyethers resulting from the polyetherification between one or more $C_2$-$C_{100}$ and preferably $C_2$-$C_{50}$ diols; (x) esters and polyesters; (xi) and mixtures thereof.

The pasty compound may be a polymer and especially a hydrocarbon-based polymer.

A preferred silicone and fluoro pasty compound is polymethyl trifluoropropyl methylalkyl dimethylsiloxane, manufactured under the name X22-1088 by Shin-Etsu.

When the pasty compound is a silicone and/or fluoro polymer, the composition advantageously comprises a compatibilizer such as short-chain esters, for instance isodecyl neopentanoate.

Among the lipid-soluble polyethers that may especially be mentioned are copolymers of ethylene oxide and/or of propylene oxide with $C_6$-$C_{30}$ alkylene oxides. Preferably, the weight ratio of the ethylene oxide and/or of the propylene oxide to the alkylene oxides in the copolymer is from 5:95 to 70:30. In this family, mention will be made especially of block copolymers comprising $C_6$-$C_{30}$ alkylene oxide blocks with a molecular weight of from 1000 to 10,000; for example a polyoxyethylene/polydodecylene glycol block copolymer such as the ethers of dodecanediol (22 mol) and of polyethylene glycol (45 oxyethylene or OE units) sold under the brand name Elfacos ST9 by Akzo Nobel.

Among the esters that are especially preferred are: (i) esters of a glycerol oligomer, especially diglycerol esters, in particular condensates of adipic acid and of glycerol, for which some of the hydroxyl groups of the glycerols have reacted with a mixture of fatty acids such as stearic acid, capric acid, isostearic acid and 12-hydroxystearic acid, for instance those sold under the brand name Softisan 649 by the company Sasol; (ii) phytosterol esters; (iii) pentaerythritol esters; (iv) esters formed from: at least one $C_{16-40}$ alcohol, at least one of the alcohols being a Guerbet alcohol, and a diacid dimer formed from at least one unsaturated $C_{18-40}$ fatty acid, for instance the ester of fatty acid dimer of tall oil containing 36 carbon atoms and of a mixture i) of Guerbet alcohols containing 32 carbon atoms and ii) of behenyl alcohol; the ester of linoleic acid dimer and of a mixture of two Guerbet alcohols, 2-tetradecyl-octadecanol (32 carbon atoms) and 2-hexadecyleicosanol (36 carbon atoms); (v) non-crosslinked polyesters resulting from polycondensation between a linear or branched $C_4$-$C_{50}$ dicarboxylic acid or polycarboxylic acid and a $C_2$-$C_{50}$ diol or polyol; (vi) polyesters resulting from esterification between a polycarboxylic acid and an aliphatic hydroxycarboxylic acid ester, for instance Risocast DA-L and Risocast DA-H sold by the Japanese company Kokyu Alcohol Kogyo, which are esters resulting from the esterification reaction of hydrogenated castor oil with dilinoleic acid or isostearic acid, and (vii) aliphatic esters of an ester resulting from esterification between and an aliphatic hydroxycarboxylic acid ester and an aliphatic carboxylic acid, for example the product sold under the trade name Salacos HCIS (V)-L sold by the company Nishing Oil.

A Guerbet alcohol is the reaction product of the Guerbet reaction, which is well known to those skilled in the art. This is a reaction that transforms a primary aliphatic alcohol into its (3-alkyl dimer alcohol with loss of one equivalent of water.

The aliphatic carboxylic acids described above generally contain from 4 to 30 and preferably from 8 to 30 carbon atoms. They are preferably selected from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof.

The aliphatic carboxylic acids are preferably branched.

The aliphatic hydroxycarboxylic acid esters are advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid esters are especially selected from:

a) partial or total esters of saturated linear monohydroxylated aliphatic monocarboxylic acids;

b) partial or total esters of unsaturated monohydroxylated aliphatic monocarboxylic acids;

c) partial or total esters of saturated monohydroxylated aliphatic polycarboxylic acids;

d) partial or total esters of saturated polyhydroxylated aliphatic polycarboxylic acids;

e) partial or total esters of $C_2$ to $C_{16}$ aliphatic polyols that have reacted with a monohydroxylated or polyhydroxylated aliphatic monocarboxylic or polycarboxylic acid, f) and mixtures thereof.

The aliphatic esters of an ester are advantageously selected from:

the ester resulting from the esterification reaction of hydrogenated castor oil with isostearic acid in proportions of 1 to 1 (1/1), known as hydrogenated castor oil monoisostearate, the ester resulting from the esterification reaction of hydrogenated castor oil with isostearic acid in proportions of 1 to 2 (1/2), known as hydrogenated castor oil diisostearate,

the ester resulting from the esterification reaction of
    hydrogenated castor oil with isostearic acid in propor-
    tions of 1 to 3 (1/3), known as hydrogenated castor oil
    triisostearate,
and mixtures thereof.

Preferably, the pasty compound is selected from com-
pounds of plant origin.

Among these compounds, mention may be made espe-
cially of isomerized jojoba oil such as the trans-isomerized
partially hydrogenated jojoba oil, orange wax, cupuacu
butter, murumuru butter, shea butter, partially hydrogenated
olive oil, cocoa butter, and mango oil.

According to one particular embodiment a composition
according to the invention comprises shea butter.

The pasty compound or compounds, if present, are pref-
erably present in the emulsion in a total amount less than 5%
by weight, less than 4% by weight, or less than 3% by
weight. The pasty compounds may be present in a total
amount greater than 0.1%, 0.5%, or 1% by weight.

In some embodiments, the emulsion is free or substan-
tially free from pasty compounds.

In some embodiments, the emulsion is free or substan-
tially free from hard waxes (waxes exhibiting a hardness
greater than 5 MPa).

Other Materials

The disclosed emulsion can generally be described as
containing water, talc, the high HLB surfactants, the pasty
compounds, and other materials. The other materials may
comprise or consist of a silicone material, a secondary filler
agent, a hygroscopic agent, solvents, thickeners, chelants,
anti-oxidants, and preservatives. In preferred embodiments,
the emulsion is free, or substantially free, of colorants,
including pigments. In preferred embodiments, the emulsion
is free, or substantially free, of other surfactants. In some
embodiments, the emulsion comprises less than 2%, or less
than 1.5%, of other surfactants.

Silicone Materials

The multipurpose eye makeup oil-in-water emulsion
according to claim 1, further comprising at least one silicone
material. The silicone material(s) preferably include non-
volatile silicone materials, such as non-volatile silicone oils.

The non-volatile silicone oils for use in the disclosed
compositions can be non-volatile polydimethylsiloxanes
(PDMS), polydimethylsiloxanes containing alkyl or alkoxy
groups, lateral and/or at the end of a silicone chain, groups
each containing from 2 to 24 carbon atoms, phenylated
silicones such as the phenyl trimethicones, phenyl dimethi-
cones, phenyl trimethylsiloxy diphenyl-siloxanes, diphenyl
dimethicones, diphenyl methyldiphenyl trisiloxanes and
2-phenylethyl trimethylsiloxysilicates. Mention may also be
made of polydimethylsiloxanes bearing dimethylsilanol end
groups known under the name dimethiconol (CTFA), such
as the oils of the 48 series from Rhodia.

Other non-volatile silicone material(s) include, e.g., sili-
cone elastomers, such as non-emulsifying silicone elasto-
mers, which include, but are not limited to, Dimethicone
Crosspolymer (INCI name), Vinyl Dimethicone Crosspoly-
mer (INCI name), Dimethicone/Vinyl Dimethicone
Crosspolymer (INCI name), and/or DimethiconeCrosspoly-
mer-3 (INCI name).

When present, the silicone materials are preferably pres-
ent in a total amount of ≤7%, ≤6%, ≤5%, or ≤4%.

Secondary Filler Agent

The emulsions may comprise one or more secondary filler
agents. For the purposes of the present disclosure, the term
"secondary filler agent" should be understood as meaning
colourless or white solid particles of any form, which are in an insoluble and dispersed form in the medium of the
composition. Secondary filler agents do not include talc.

These fillers, of mineral or organic, natural or synthetic
nature, give the composition containing them softness and
give the makeup result a matt effect and uniformity.

Among the mineral fillers that may be used in the com-
positions according to the invention, mention may be made
of natural or synthetic mica, kaolin, stearalkonium hectorite
natural or synthetic sericite, silica, hydroxyapatite, boron
nitride, calcium carbonate, hollow silica microspheres
(Silica beads from Maprecos), glass or ceramic microcap-
sules; composites of silica and titanium dioxide, such as the
TSG series sold by Nippon Sheet Glass, and mixtures
thereof.

Among the organic fillers that may be used in the com-
positions according to the invention, mention may be made
of polyamide powders (Nylon® Orgasol from Atochem),
poly-β-alanine powder and polyethylene powder, polytet-
rafluoroethylene (Teflon®) powder, lauroyllysine, tetrafluo-
roethylene polymer powders, spherical powders of cross-
linked elastomeric organopolysiloxane, described especially
in document JP-A-02-243612, such as those sold under the
name Trefil Powder E 2-506C or DC9506 or DC9701 by the
company Dow Corning, silicone resins, which are products
of hydrolysis and polycondensation of siloxane mixtures of
formulae $(R)3SiOHCH3$ and $Si(OCH3)4$, R representing an
alkyl group containing from 1 to 6 carbon atoms (for
example KSP 100 from Shin-Etsu), silicone resin micro-
beads (for example Tospearl® from Toshiba), Polypore®
L200 (Chemdal Corporation), polyurethane powders, in
particular crosslinked polyurethane powders comprising a
copolymer, the said copolymer comprising trimethylol hexyl
lactone, for instance the polymer of hexamethylene diiso-
cyanate/trimethylol hexyl lactone, sold under the name
Plastic powder D-400® or Plastic Powder D-800® by the
company Toshiki, and mixtures thereof.

Among the other organic fillers that may be used in the
compositions according to the invention, mention may be
made of starch-based or cellulose-based powders. Examples
of such fillers that may be mentioned include the Dry Flo
products sold by Akzo Nobel.

Advantageously, the fillers in accordance with the inven-
tion are mineral fillers, preferably chosen from mica, seric-
ite, kaolin, and silica, and mixtures thereof.

If present, the emulsion will contain a total amount of the
secondary filler agents that is less than the amount of talc
that is present. For example, if the emulsion comprises 20%
talc, the secondary filler agent(s) will be present in a total
amount less than 20%. In preferred embodiments, the emul-
sion comprises less than 5%, less than 3%, or less than 2%
of the secondary filler agent. In preferred embodiments, the
emulsion is free, or substantially free, of secondary filler
agents.

Hygroscopic Agent

The emulsion may also utilize hygroscopic agents. The
hygroscopic agents are preferably humectants. Humectants
suitable for use in emulsions presently disclosed include
glycerin, sodium hyaluronate, panthenol, urea, hydroxyethyl
urea, PEG/PPG/polybutylene glycol-8/5/3 glycerin, hydro-
lyzed hyaluronic acid, niacinamide, mannose, myristyl
malate phosphonic acid, biosaccharide gum, and combina-
tions thereof. In some embodiments, two or more hygro-
scopic agents are present. In some embodiments, only two
hygroscopic agents are present. In some embodiments, only
three hygroscopic agents are present.

If sodium hyaluraonate is present, it is preferably present in an amount less than 2% by weight, or less than 1% by weight.

The hygroscopic agents are advantageously present at a concentration, by weight, of about 0.01% to about 1%, or alternatively 0.1% to alternatively about 10%, or alternatively about 1% to about 7.5%, based upon weight of the emulsion Solvents The emulsion may comprise solvents, such as Representative suitable solvents include non-polar volatile hydrocarbon-based oils include isodecane and isododecane, and for example, the oils sold under the trade names Isopar™ or Permythyl®. Preferably, the volatile oils have a flash point of at least 40° C.

Other exemplary organic solvents are non-volatile solvents which include polyalphaolefins such as hydrogenated polydecene, hydrogenated C6-14 olefin polymers and polydecene.

Other suitable solvents include polyols, such as caprylyl glycol.

Other suitable solvents include esters of benzoic acid and long-chain alcohols. Preferably, the alcohols having carbon chains of between 8 and 22. Examples include, e.g., C12-15 alkyl benzoate.

Solvents are preferably present in the emulsion in total amounts less than 5% by weight, less than 4% by weight, or less than 3% by weight.

Thickeners

The emulsion may also comprise one or more thickeners, including gums (such as xanthan gum), polymers, or copolymers. Such thickeners may include, e.g., crosslinked thickening polymers comprising about 60% to about 95% by weight of acrylic acid (hydrophilic unit), about 4% to about 40% by weight of C10-C30 alkyl acrylate (hydrophobic unit), and about 0% to about 6% by weight of crosslinking polymerizable monomer. In yet further embodiments, the crosslinked thickening polymers may comprise about 96% to about 98% by weight of acrylic acid (hydrophilic unit), about 1% to about 4% by weight of C10-C30 alkyl acrylate (hydrophobic unit), and about 0.1% to 0.6% by weight of crosslinking polymerizable monomer, such as those described above. Examples of such polymers include acrylate/C10-C30 alkyl acrylate copolymers (INCI name: Acrylates/C10-30 Alkyl Acrylate Crosspolymer), such as the products sold by Lubrizol under the trade names PEMULEN™ TR1, PEMULEN™ TR2, CARBOPOL® 1382 and CARBOPOL® EDT 2020 may be chosen.

In further embodiments, the thickener may be chosen from nonionic homopolymers or copolymers containing ethylenically unsaturated monomers of the ester and/or amide type. For example, the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

Further non-limiting examples of thickeners include polyacrylamide (and) C13-14 isoparaffin (and) laureth-7 (such as Sepigel™ 305 from Seppic), acrylates/C10-30 alkyl acrylate crosspolymer (such as Carbopol® Ultrez 20 polymer from Lubrizol), acrylates/C10-30 alkyl acrylate crosspolymer (such as Permulen™ TR-1 from Lubrizol), and polyacrylate crosspolymer-6 (such as Sepimax Zen from Seppic).

In a preferred embodiment, the thickener includes cross- or co-polymers of polyacryloyl/taurate or polyacryloyl/dimethyltaurate. Non-limiting examples of such polymers include ammonium acryloyldimethyltaurate/steareth-25 methacrylatecrosspolymer, ammonium acryloyldimethyltaurate/steareth-8 methacrylate copolymer, ammonium acryloyldimethyltaurate/beheneth-25 methacrylate crossopolymer, and ammoniumacryloyldimethyltaurate/laureth-7 methacrylate copolymer, and mixtures thereof.

In preferred embodiments, the thickeners consist of a gum and a cross- or co-polymers of polyacryloyl/taurate or polyacryloyl/dimethyltaurate.

In some embodiments, the thickeners are present in the emulsion in a total amount of between 0.1% and 2% by weight, such as between 0.1% and 1.5%. In some embodiments, the thickeners are present in amounts≤2%, ≤1.75%, ≤1.5%, ≤1.25%, or ≤1%.

Preservatives

The oil-in-water emulsions of the present disclosure will typically comprise an appropriate preservative, such as phenoxyethanol.

Also disclosed is an eye makeup kit. The kit comprises (i) the multipurpose eye makeup oil-in-water emulsion as described previously, as well as (ii) an eyeshadow composition, a mascara composition, or a combination thereof.

Any appropriate eyeshadow and/or mascara composition known to those of skill in the art may be used.

Common eyeshadow products comprise fillers (such as talc, clays, mica, etc.), binders (such as those comprising zinc, magnesium, etc.), preservatives, slip agents (such as silica, nylon, dimethicone, etc.), and a colorant (such as iron oxides, etc.). Eyeshadow products may also include one or more of the following: ascorbyl palmitate, beeswax, benzyldimethylstearylammonium hectorite, BHT, bismuth oxychloride, C12-C15 alkyl benzoate, calcium silicate, candelilla wax, caprylic/capric acid tryglyceride, carnauba wax, chromium hydroxide green, chromium oxide greens iron oxides, citric acid, coco caprylate caprate, D1 tocopherol, hydrogenated oil, hydroxylated lanolin, imidazolidinyl urea, isopropyl triisostearoyl titanate, lauroyl lysine, lauryl lysine, lecithin, lipophilic glyceryl monostearate, magnesium carbonate, manganese violet, methyl polysiloxane, mica, mineral oil, octyldodecyl stearoyl stearate, paraffin, parahydroxybenzoate ester, polymethyl methacrylate, polyvinylidene copolymer, propylene carbonate, quaternium-15, saturated fatty acid glycerides, sodium dehydroacetate, soybean phospholipid soybean lecithin, stearic acid, titanium dioxide, trilaurin, trioctanion, ultramarines, zinc oxides, iron oxides, ferric ferrocyamide, ferric ammonium ferrocyamide, carmine, polyglyceryl-3 diisostearate, hydrogenated coco-glycerides, ethylene/methacrylate copolymer, nylon-12, pentahydrosqualene, acrylates copolymer, polyglycery-4 isostearate, laurylmethicone copolyol, perfluoropolymethyliospropeth phosphate, butylparaben, phenoxyethanol and/or various coloring agents.

Common mascara products comprise colorants (such as iron oxides, carbon black, etc.), waxes (such as beeswax, paraffin, etc.), thickening polymers (such as gums and cellulose-based thickeners), film formers, and other additives. Mascara products may also include one or more of the following: mica, TEA-stearate, glyceryl stearate, tricontanyl PVP, silk powder, diglycol/CHDM/lsophthalates/sip copolymer, PTFE, stearate, sorbitan laurate, polysorbate 20, acacia, acrylates copolymer, alcohol denatured, aminomethyl propandiol, ammonium acrylates copolymer, ammonium hydroxide, ammonium lanolate, ascorbyl palmitate, benzyl alcohol, BHA, butyl stearate, C9-11 isoparaffin, candelilla wax, carmine, cetyl alcohol, cetyl stearate, chromium hydroxide green, citric acid, cyclomethicone, ethylparaben, fragrance, glycerin, glyceryl rosinate, hydrolyzed keratin, hydroxyethylcellulose, imidazolidinyl urea, iron oxides, kaolin, magnesium aluminum silicate, methyl ethyl propyl butylparabens/phenoxyethanol, MIPA-lanolate, MIPA-oleate, nnoxynol-10, oleic acid, oleyl alcohol, PEG-100 stearate, pentaerythrityl tetrastearate, phenoxyethanol, polybutene, polyethylene, polyquaternium 10, polyvinyl alcohol, potassium Ocotxynol-12, phosphate, propylene carbonate, propylene glycol, propyl, quaternium-15, quaternium-18, hectorite, quaternium-22, SD alcohol 40-B, silica, silk powder, sodium dehydroacetate, sodium laureth sulfate, sodium lauryl sulfate, sodium polymethacrylate, sorbitan sesquioleate, talc, titanium dioxide, triclosan, trimethylsiloxysilicate, trisodium EDTA, ultramarines and/or xanthan gum.

Also disclosed is a method for priming eyelids, eyelashes, or both. A multipurpose eye makeup oil-in-water emulsion as disclosed previously is provided. The emulsion is then applied to an eyelid, eyelashes, or both. In some embodiments, the emulsion is applied to both an eyelid and eyelashes. In various other embodiments, once the emulsion has been applied, an eyeshadow composition is then applied to the eyelid over the emulsion. In other embodiments, once the emulsion has been applied, a mascara composition to the eyelashes over the emulsion. In some embodiments, both a mascara and an eyeshadow are applied to the eyelashes and eyelids, respectively, after the emulsion has been applied.

Example

The present invention will be described in a more detailed manner by way of examples. However, these examples should not be construed as limiting the scope of the present invention. The examples below are presented as non-limiting illustrations in the field of the invention.

Preparations

The following compositions according to Example 1 (Ex. 1) and Comparative Example 2 (Comp. Ex 2), shown in Table 1, were prepared by mixing the components shown in Table 1. Specifically, the Phase A ingredients were added to a first vessel and heated to 65 C/75 C while being mixed until homogenous, then set aside. The Phase B ingredients were then added to a new vessel and heated to 65 C/75 C and being mixed until homogenous. Phase A is then added to Phase B, and emulsified. The composition is then cooled to 45 C/50 C and Phase C was added with strong homogenization with rotor stator at 2500 rpm for at least 15 min. The composition was then further cooled to 25 C/30 C and Phase D was added while being mixed until homogeneous. Once completed, the composition then transferred as appropriate. The numerical values for the amounts of the components shown in Table 1 are all based on "% by weight".

TABLE 1

| | Ex. 1 | Comp. Ex. 2 |
|---|---|---|
| Phase A | | |
| High HLB Surfactants | 3-8 | 1-3 |
| Other Surfactants | 0.1-2 | 3-6 |
| Pasty Compounds | 0.1-4 | 2-5 |
| Oil-based solvents | 0.1-3 | 0.1-3 |
| Phase B | | |
| Water | 50-70 | 50-70 |

TABLE 1-continued

| | Ex. 1 | Comp. Ex. 2 |
|---|---|---|
| Thickeners | 0.1-1.5 | 2-5 |
| Hygroscopic Agent | 5-8 | 5-8 |
| Water-based solvents | 0.1-3 | 0.1-3 |
| Secondary Filler Agents | 0.1-1 | 0.1-1 |
| Chelants | 0.1-1 | 0.1-1 |
| Anti-oxidants | 0.1-1 | 0.1-1 |
| Preservatives | 0.1-1 | 0.1-1 |
| Phase C | | |
| Silicone Materials | 0.1-5 | 7-11 |
| Phase D | | |
| Talc | 10-20 | 10-20 |

The evaluation results for a standard eyeshadow composition, using the example and comparative formulas as a base or primer, are summarized in Table 2. The formulations were evaluated based on their shine and intensity after application of the eyeshadow, and the evenness of the eyeshadow after 8 hours of wear, as compared to use of the standard eyeshadow composition without the base or primer. The results are from a trained sensory panel of mascara and eyeshadow users, involving descriptive sensory profiles from 16 Caucasian women with normal to combination skin.

TABLE 2

| Evaluation | Ex. 1 | Comp. Ex. 2 |
|---|---|---|
| Application (Shine) | = | = |
| Application (Intensity) | + | = |
| 8 Hour Wear (Evenness) | + | = |

As Table 2 shows, neither the example nor comparative formulation improved the shine of the application. However, the intensity was clearly rated higher with the exemplary formula, as compared to the comparative formulation or the eyeshadow without a base or primer. Similarly, the 8-hour wear showed clearly higher ratings for evenness as compared to the comparative formulation or the eyeshadow without a base or primer.

Those skilled in the art will recognize or be able to ascertain using no more than routine experimentation, many equivalents to the specific embodiments of the invention described herein. Such equivalents are intended to be encompassed by the following claims.

What is claimed is:

1. A method for priming eyelids, eyelashes, or both, comprising:

providing a multipurpose eye makeup oil-in-water emulsion consisting of:

water;

an ester of benzoic acid and long-chain alcohols in an amount of no more than 3% by weight of the multipurpose eye makeup oil-in-water emulsion;

a humectant in an amount of 1-7.5% by weight of the multipurpose eye makeup oil-in-water emulsion;

a silicone oil in an amount of no more than 7% by weight of the multipurpose eye makeup oil-in-water emulsion;

talc in an amount of at least 10% by weight of the multipurpose eye makeup oil-in-water emulsion;

a plurality of high HLB surfactants in an amount of 3-15% by weight of the multipurpose eye makeup oil-in-water emulsion, the plurality of high HLB surfactants being fatty alcohols and/or fatty esters of PEG or glycerol, where at least one of the plurality of high HLB surfactants comprises a fatty ester of PEG that includes a diester of stearic acid; and optionally a secondary filler agent, a hygroscopic agent, an additional solvent, a thickener, a chelant, an anti-oxidant, a preservative, or a combination thereof; and applying the multipurpose eye makeup oil-in-water emulsion to an eyelid, eyelashes, or both.

2. The method of claim 1, wherein the multipurpose eye makeup oil-in-water emulsion is applied to both an eyelid and eyelashes.

3. The method of claim 1, further comprising applying an eyeshadow composition to the eyelid over the multipurpose eye makeup oil-in-water emulsion.

4. The method of claim 1, further comprising applying a mascara composition to the eyelashes over the multipurpose eye makeup oil-in-water emulsion.

5. The method of claim 1, wherein the multipurpose eye makeup oil-in-water emulsion comprises between 10% and 20% by weight of talc.

* * * * *

14